US012208373B2

(12) United States Patent
Simanzhenkov et al.

(10) Patent No.: US 12,208,373 B2
(45) Date of Patent: Jan. 28, 2025

(54) CALCINATION PROCESS TO PRODUCE ENHANCED ODH CATALYST (71) Applicant: NOVA Chemicals (International) S.A., Fribourg (CH)

(72) Inventors: Vasily Simanzhenkov, Calgary (CA); Xiaoliang Gao, Calgary (CA); David Sullivan, Calgary (CA); Yipei Styles, Calgary (CA); Yoonhee Kim, Calgary (CA); Hanna Drag, Calgary (CA); Marie Barnes, Calgary (CA)

(73) Assignee: NOVA Chemicals (International) S.A., Fribourg (CH)

( * ) Notice: Subject to any disclaimer, the term of this patent is extended or adjusted under 35 U.S.C. 154(b) by 1 day.

(21) Appl. No.: 18/303,236

(22) Filed: Apr. 19, 2023

(65) Prior Publication Data
US 2023/0271162 A1 Aug. 31, 2023

Related U.S. Application Data (62) Division of application No. 17/236,669, filed on Apr. 21, 2021, now Pat. No. 11,654,419, which is a (Continued)

(30) Foreign Application Priority Data

Mar. 26, 2018 (CA) ................. CA 2999092

(51) Int. Cl.
*B01J 23/00* (2006.01)
*B01J 6/00* (2006.01)
*B01J 27/057* (2006.01)
*B01J 35/00* (2024.01)
*B01J 35/30* (2024.01)
*B01J 35/50* (2024.01)
*B01J 35/58* (2024.01)
*B01J 37/00* (2006.01)
*B01J 37/04* (2006.01)
*B01J 37/08* (2006.01)
*B01J 37/10* (2006.01)
*B01J 38/12* (2006.01)
*C07C 5/42* (2006.01)
*C07C 5/48* (2006.01)

(52) U.S. Cl.
CPC ............. *B01J 23/002* (2013.01); *B01J 6/001* (2013.01); *B01J 27/0576* (2013.01); *B01J 35/19* (2024.01); *B01J 35/30* (2024.01); *B01J 35/393* (2024.01); *B01J 35/50* (2024.01); *B01J 35/58* (2024.01); *B01J 37/0009* (2013.01); *B01J 37/08* (2013.01); *B01J 37/10* (2013.01); *C07C 5/42* (2013.01); *C07C 5/48* (2013.01); *B01J 37/0036* (2013.01); *B01J 37/04* (2013.01); *B01J 38/12* (2013.01); *B01J 2523/00* (2013.01); *B01J 2523/55* (2013.01); *B01J 2523/56* (2013.01); *B01J 2523/64* (2013.01); *B01J 2523/68* (2013.01); *C07C 2523/20* (2013.01); *C07C 2523/22* (2013.01); *C07C 2523/28* (2013.01); *C07C 2527/057* (2013.01)

(58) Field of Classification Search
CPC ........ B01J 37/084; B01J 23/002; B01J 6/001; B01J 27/0576; B01J 23/22; B01J 23/28; B01J 35/006; B01J 35/026; B01J 35/06; B01J 37/0009; B01J 37/08; B01J 37/10; B01J 2523/00; B01J 2523/55; B01J 2523/56; B01J 2523/64; B01J 2523/68; B01J 2208/00017; B01J 2208/00548; B01J 2208/00539; B01J 2208/00796; B01J 2219/00051; B01J 2219/00162; B01J 2219/00164; B01J 2219/0254; B01J 2219/0263; B01J 2219/0286; C07C 2523/20; C07C 2523/22; C07C 2523/28; C07C 2527/057
USPC .................. 502/311, 312; 585/616, 654, 661
See application file for complete search history.

(56) References Cited

U.S. PATENT DOCUMENTS 4,250,346 A  2/1981 Young et al.
6,841,699 B2  1/2005 Bogan et al.
(Continued)

FOREIGN PATENT DOCUMENTS

CA    2752409 A1   3/2013
CN  101616732 A   12/2009
(Continued)

OTHER PUBLICATIONS

ASTM E2945-14; Standard Test Method for Film Permeability Determination Using Static Permeability Cells; Copyright ASTM International; Current edition approved Feb. 1, 2014, Published Apr. 2014, pp. 1-12.

Primary Examiner — Patricia L. Hailey
(74) Attorney, Agent, or Firm — Fish & Richardson P.C.

(57) ABSTRACT

Mixed metal oxide catalysts having an amorphous content of not less than 40 wt. % are prepared by calcining the catalyst precursor fully or partially enclosed by a porous material having a melting temperature greater than 600° C. in an inert container including heating the catalyst precursor at a rate from 0.5 to 10° C. per minute from room temperature to a temperature from 370° C. to 540° C. under a stream of pre heated gas chosen from steam and inert gas and mixtures thereof at a pressure of greater than or equal to 1 psig having a temperature from 300° C. to 540° C. and holding the catalyst precursor at that temperature for at least 2 hours and cooling the catalyst precursor to room temperature.

18 Claims, 4 Drawing Sheets

Related U.S. Application Data division of application No. 16/358,802, filed on Mar. 20, 2019, now Pat. No. 11,014,072.

(56) References Cited

U.S. PATENT DOCUMENTS

| | | |
|---|---|---|
| 7,319,179 B2 | 1/2008 | Lopez et al. |
| 7,919,428 B2 | 4/2011 | Sutradhar et al. |
| 8,846,996 B2 * | 9/2014 | Kustov ................ B01J 23/002 |
| | | 502/151 |
| 10,350,582 B2 | 7/2019 | Simanzhenkov et al. |
| 10,661,256 B2 | 5/2020 | Kim et al. |
| 11,654,419 B2 | 5/2023 | Simanzhenkov et al. |
| 2002/0038052 A1 | 3/2002 | Bogan et al. |
| 2010/0256432 A1 | 10/2010 | Arnold et al. |
| 2011/0245571 A1 | 10/2011 | Kustov et al. |
| 2012/0016171 A1 | 1/2012 | Kustov et al. |
| 2015/0119622 A1 | 4/2015 | De et al. |
| 2016/0207035 A1 | 7/2016 | Zander et al. |
| 2017/0361309 A1 | 12/2017 | Simanzhenkov et al. |
| 2018/0021760 A1 | 1/2018 | Simanzhenkov et al. |
| 2019/0039050 A1 | 2/2019 | Gao et al. |
| 2019/0291080 A1 | 9/2019 | Simanzhenkov et al. |
| 2021/0237036 A1 | 8/2021 | Simanzhenkov et al. |

FOREIGN PATENT DOCUMENTS

| | | |
|---|---|---|
| DE | 102013014241 | 3/2015 |
| WO | WO2018198015 | 11/2018 |

* cited by examiner

CALCINATION PROCESS TO PRODUCE ENHANCED ODH CATALYST

This application is a divisional of and claims the benefit of priority to U.S. patent application Ser. No. 17/236,669, filed on Apr. 21, 2021, which is a divisional of and claims the benefit of priority to U.S. patent application Ser. No. 16/358,802, filed on Mar. 20, 2019, which claims the benefit of the earlier filing date of Canadian application serial number CA 2 999 092 filed on Mar. 26, 2018, the contents of which are incorporated herein by reference in their entirety.

The present disclosure relates to a controlled calcination process to produce an enhanced catalyst for the oxidative dehydrogenation for paraffins to olefins, particularly lower paraffins such as $C_{2-4}$ paraffins to the corresponding olefins. Mixed metal oxide catalysts for the dehydrogenation of paraffins have been known since the mid to late 1960's. The catalyst activity and selectivity depend more on the content of amorphous phase (sometimes referred to as the M2 phase) versus crystalline phase(s) (sometimes referred to as M1 phase) of the catalyst.

Over about the past 10 years there has been increasing interest in the mixed metal oxide catalyst including Mo, V, Nb and one or more of Te and Sb optionally together with one or more of Pd, Sb Ba, Al, W, Ga, Bi, Sn, Cu, Ti, Fe, Co, Ni, Cr, Zr, and Ca.

In some embodiments the present disclosure provides a method to calcine a mixed metal oxide oxidative dehydrogenation catalyst. In some embodiments of the present disclosure amorphous content remains high, for example greater than 40 wt. %, or for example above 50 wt. %.

In some embodiments, the present disclosure provides a method to calcine a catalyst precursor of the formula $Mo_1V_{0.1-1}Nb_{0.1-1}Te_{0.01-0.2}X_{0-2}O_d$ where X is chosen from Pd, Sb Ba, Al, W, Ga, Bi, Sn, Cu, Ti, Fe, Co, Ni, Cr, Zr, Ca and oxides thereof and mixtures thereof, and d is a number to satisfy the valence of the catalyst while maintaining an amorphous content of not less than 40 wt. %, the method including: Calcining the catalyst precursor in an inert container with flow passage there through, including heating the catalyst precursor at a rate from 0.5 to 10° C. per minute from room temperature to a holding temperature from 370° C. to 540° C. under a stream of pre heated gas chosen from steam and inert gas and mixtures thereof at a rate of flow comparable to a flow rate of not less 150 sccm through a 2.54 cm diameter tube, with a length of 152 cm at a pressure of greater than or equal to 1 psig having a temperature of at least 100° C. in some embodiments from 300° C. to 540° C. and holding the catalyst precursor at the holding temperature for at least 2 hours and cooling the catalyst precursor to room temperature said catalyst precursor being fully or partially enclosed by a porous material having a melting temperature greater than 600° C.

In a further embodiment, the inert container is made from high temperature glass (e.g. Pyrex), quartz, ceramics (Beryllium Oxide), alumina), or steel.

In a further embodiment, the inert container has a heat conductivity greater than 0.34 W·m$^{-1}$·K.

In a further embodiment, the flow rate of preheated gas is greater than 150 sccm.

In a further embodiment, the pressure of inert gas greater than 1 psig.

In a further embodiment the heat up rate is 0.9 to 2.0 C per min.

In a further embodiment, the catalyst precursor is held at the holding temperature from 2 to 24 hours.

In a further embodiment, the holding temperature is from 400° C. to 525° C.

In a further embodiment, the inert gas includes nitrogen.

In a further embodiment, the porous material is chosen from glass and mineral fiber.

In a further embodiment, optionally charcoal or activated carbon is on the outer surface of the porous material in an amount up to 0.5 g per 1 g of catalyst precursor.

In a further embodiment X is one or more metals and oxides thereof chosen from Pd, Sb, Ba, Al, Cu, Ti, Fe, Ca, Zr and mixtures thereof.

In a further embodiment the molar ratio of said one or more metals and oxides chosen from Pd, Sb, Ba, Al, Cu, Ti, Fe, Ca, Zr and mixtures thereof to Mo is from 1:0.001 to 0.3, for example, from 1:0.05 to 0.15.

In a further embodiment X is chosen from one or more metals and oxides thereof are chosen from Pd, Sb, Ba, Al, Cu and mixtures thereof. In a further embodiment in the catalyst, precursor X is absent.

In a further embodiment, the catalyst precursor has the formula:

$Mo_{1.0}V_{0.10-0.49}Te_{0.06-0.17}Nb_{0.13-0.19}O_d$.

In a further embodiment, the calcined catalyst has the formula:

$Mo_1V_{0.40-0.45}Te_{0.10-0.16}Nb_{0.13-0.16}O_d$.

In a further embodiment, the calcined catalyst has the formula $MoV_{0.40-0.45}Te_{0.10-0.16}Nb_{0.13-0.16}O_d$.

having an amorphous content of not less than 40 wt. %.

In a further embodiment, the calcined catalyst has a crystallite size calculated according to the Scherrer equation of 45 to 55 nm.

In a further embodiment, the calcined catalyst has a crystallite size calculated according to the Scherrer equation of 50 to 52 nm.

In a further embodiment, the calcined catalyst is bound, agglomerated, filled, promoted, impregnated, or supported with from 5-90, wt. % of a material other than active phase.

A further embodiment provides a method for the oxidative dehydrogenation of a mixed feed including one or more $C_{2-4}$ paraffins and oxygen in a volume ratio from 70:30 to 95:5 and optionally one or more $C_{3-6}$ alkanes or alkenes and oxygenated species including CO and $CO_2$ at a temperature from 320° C. up to 385° C., a gas hourly space velocity of not less than 100 hr$^{-1}$, and a pressure from 0.8 to 7 atmospheres including passing said mixture over the above catalyst (s).

NUMBERS RANGES

Other than in the operating examples or where otherwise indicated, all numbers or expressions referring to quantities of ingredients, reaction conditions, etc. used in the specification and claims are to be understood as modified in all instances by the term "about. Accordingly, unless indicated to the contrary, the numerical parameters set forth in the following specification and attached claims are approximations that can vary depending upon the properties that the present disclosure desires to obtain. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical values, however, inherently contain certain errors necessarily resulting from the standard deviation found in their respective testing measurements.

Also, it should be understood that any numerical range recited herein is intended to include all sub-ranges subsumed therein. For example, a range of "1 to 10" is intended to include all sub-ranges between and including the recited minimum value of 1 and the recited maximum value of 10; that is, having a minimum value equal to or greater than 1 and a maximum value of equal to or less than 10. Because the disclosed numerical ranges are continuous, they include every value between the minimum and maximum values. Unless expressly indicated otherwise, the various numerical ranges specified in this application are approximations.

All compositional ranges expressed herein are limited in total to and do not exceed 100 percent (volume percent or weight percent) in practice. Where multiple components can be present in a composition, the sum of the maximum amounts of each component can exceed 100 percent, with the understanding that, and as those skilled in the art readily understand, that the amounts of the components actually used will conform to the maximum of 100 percent.

In the specification, the phrase the temperature at which there is 25% conversion of ethane to ethylene is determined by plotting a graph of conversion to ethylene against temperature typically with data points below and above 25% conversion or the data is fit to an equation and the temperature at which there is a 25% conversion of ethane to ethylene is determined. In some instances, in the examples the data had to be extrapolated to determine the temperature at which 25% conversion occurred.

In the specification, the phrase selectivity at 25% conversion is determined by plotting the selectivity as function of temperature or fit to an equation. Then having calculated the temperature at which 25% conversion occurs one can determine either from the graph or from the equation the selectivity at that temperature.

The ratio of amorphous component to crystalline component may be determined by obtaining an XRD for the calcined catalyst. Within 24 hours of obtaining the sample XRD a standard (100% crystalline material such as Corundum) is run on the XRD instrument to determine the K factor for the instrument. Then knowing the K factor the percentage of crystalline phase per unit mass of sample and the difference is the weight of the amorphous content per unit mass of sample is determined. Such as disclosed in O. Connor and Raven (1988), Powder Diffraction, 3(1), 2-6; http://www.icdd.com/ppxrd/12/presentations/P30-Arnt-Kern-ppxrd-12.pdf.

A typical procedure is as follows:
1. The sample is finely ground to reduce particle size to less than 250 microns and obtain a uniform mixture.
2. The ground sample is loaded onto an XRD sample holder preferably having an EDS stub for XRD and EDS analysis.
3. Acquire the XRD spectrum and where applicable perform EDS analysis using a scanning electron microscope (SEM).
4. Combine Highscore Plus, EDS and Rietveld Refinement to perform qualitative and quantitative analysis.
5. Amorphous analysis—Run standard using exactly same holder and same program as with the sample. Standard must be run with 24 hrs after the sample was run.
6. Using external standard method to determine the amorphous content.
7. With an external standard method an instrument intensity constant often called K-factor (sometimes called G-factor as well) is determined. The instrument and software already have a program set up for this method.
8. Generate report.

In this specification non-antagonistic binder means a binder other than $Nb_2O_5$ which when incorporated into the agglomerated catalyst has less than a 5% antagonistic effect on the agglomerated catalysts. Some non-antagonistic binders include oxides of aluminum, titanium and zirconium. Silica oxides have an antagonistic effect on the agglomerated catalysts and the catalyst active sites.

The Catalyst Precursor The catalyst precursor may be prepared using a hydrothermal process including following steps:
i) forming an aqueous solution of ammonium heptamolybdate (tetrahydrate) and telluric acid in a molar ratio of Mo:Te of 1:0.14 to 0.20, in some instances from 1:0.17, at a temperature from 30° C. to 85° C. and adjusting the pH of the solution to 6.5 to 8.5, for example, from 7.0 to 8.0, for example, from 7.3 to 7.7, for example, with a nitrogen-containing base to form soluble salts of the metals;
ii) stirring the pH adjusted solution for a time of not less than 15 minutes, in some instances from not less than 2 hours, in some instances not more than 4 hours;
iii) adjusting the pH of the resulting solution to from 4.5 to 5.5, for example, from 4.8 to 5.2, for example from 5.0 to 5.2 with an acid, for example, sulfuric acid (0.01-18 M, typically 2-18 M) and stir the resulting solution at a temperature of 80° C. until it is homogeneous in some instances with a stirring time up to 30 minutes; In some circumstances, to maintain 80° C. temperature, a cooling device needs to be used to maintain temperature at 80° C.
iv) preparing an aqueous solution of vanadyl sulphate at a temperature from room temperature to 80° C. (for example, 50° C. to 70° C., for example, 55° C. to 65° C.);
v) mixing the solutions from steps i) and iv) together to provide a molar ratio of V:Mo from 1.00-1.67 to 1 in some cases from 1.45-1.55 to 1.00; vi) preparing a solution of $H_2C_2O_4$ and $Nb_2O_5 \times H_2O$ in a molar ratio from 5.0 to 6:0, in some instances 5.0-5.3:1;
vii) slowly (i.e. dropwise) adding the solution from step vi) to the solution of step vi) to provide molar ratio of Nb:Mo from 5.56-7.14:1 in some instances from 6.20-6.40 to form a slurry (typically the addition is at temperatures between 20° C. and 80° C.; for example, 20° C. to 30° C.); and vii) heating the resulting slurry in an autoclave under an inert gas, air, carbon dioxide, carbon monoxide and mixtures thereof at a pressure of not less than 1 psig and at a temperature from 140° C. to 190° C. for not less than 6 hours, or for example, not less than 6 hours and not more than 36.

The temperature for the hydrothermal treatment may range from 140° C. to 180° C., in some embodiments from 145° C. to 175° C.

The pressure in the autoclave may range from equal or above the saturated water vapor pressure at the corresponding reaction temperature in some embodiments from 30 to 200 psig (206 kPag to 1375 kPag), in some embodiments from 55 psig (380 kPag) to 170 psig (1170 kPag) above atmospheric pressure.

The gaseous product species can be vented from the autoclave (reactor).

Optionally there is a condenser upstream of the autoclave outlet which may be operated at a temperature above 0° C. and below reaction temperature.

In some embodiments, the pressure inside the autoclave may be maintained above atmospheric using a liquid filled column or bubbler or a pressure regulator valve.

In some embodiments, the hydrothermal treatment may be from 6 to 15 hours.

In some embodiments, the autoclave (reactor) is allowed to cool to room temperature, typically overnight. The reactor contents are filtered using a Buchner filter and washed with (distilled) water or an aqueous oxalic acid solution and dried in an oven for not less than 6 hours at a temperature from 70° C. to 120° C.

In some embodiments, the precatalyst is separated from the aqueous phase, for example, by filtration or evaporation, and washed with (distilled or deionized) water and dried in an oven for not less than 6 hours at a temperature from 70° C. to 120° C. The precatalyst may be dried in an atmosphere including one or more inert gases. In some instances, optionally, the dried precatalyst may be ground using mechanical means (e.g. a ball or roller mill) or the dried precatalyst could be subject to cryogenic grinding. The dried and ground precatalyst may in some instances be subject to sieving through a small particle size sieve to obtain a fraction having a particle size less than 250 microns, for example, less than 125 microns.

In some embodiments, the product from the hydrothermal treatment is treated with from 0.3-2.5 mL of a 30 wt. % solution of aqueous $H_2O_2$ per gram of catalyst precursor.

In some embodiments, the catalyst precursor (i.e. prior to calcining) has the formula:

$Mo_1V_{0.1-1}Nb_{0.1-1}Te_{0.01-0.2}X_{0-2}O_d$ where X is chosen from Pd, Sb Ba, Al, W, Ga, Bi, Sn, Cu, Ti, Fe, Co, Ni, Cr, Zr, Ca and oxides and mixtures thereof, and d is a number to satisfy the valence of the catalyst precursor. In some embodiments X is chosen from Pd, Sb, Ba, Al, Cu, Ti, Fe, Ca, Zr and mixtures thereof. In some embodiments, X is chosen from Pd, Sb, Ba, Al, Cu and mixtures thereof. In the formula for the precursor the molar ratio of said one or more metals and oxides and mixtures thereof to Mo is up to 2, typically if X is present from 0.001-0.3, for example, from 0.05-0.15.

In some embodiments, X is absent from the catalyst precursor and it has the formula:

$Mo_{1.0}V_{0.10-0.49}Te_{0.06-0.17}Nb_{0.13-0.19}O_d$ where d is a number to satisfy the valence of the catalyst precursor.

In some embodiments, the reactor is allowed to cool to room temperature, typically overnight. The reactor contents were filtered using a Buchner filter and washed with (distilled) water or an aqueous oxalic acid solution and dried in an oven for not less than 6 hours at a temperature from 70° C. to 120° C. The dried precatalyst can be ground, typically to a size less than 250 μm and calcined in an inert atmosphere such as nitrogen for a time from 1 to 20 hours.

The catalyst precursor can be calcined in an inert container with a flow passage there through, including heating the catalyst precursor at a rate from 0.5 to 10° C. per minute in some embodiments from 0.9 to 2 C per minute from room temperature to a temperature from 300° C. to 540° C., in some cases from 400° C. to 525° C., under a dynamic stream of optionally preheated inert gas such as nitrogen, helium, etc. and mixtures thereof at a flow rate of nitrogen comparable to (based upon) a flow of nitrogen through a 1 inch internal diameter tube having a length of 152 cm (59.8 inches) at a flow rate from 200-500 sccm per 30-250 gram of catalyst precursor.

The inert container may have a heat conductivity greater than 0.34 $Wm^{-1} \cdot K^{-1}$, in some embodiments from 1.2 $W \cdot m^{-1} \cdot K^{-1}$ to 50 $W \cdot m^{-1} \cdot K^{-1}$. The container may be made from high temperature glass (e.g. Pyrex), quartz, ceramics (e.g. beryllium oxide), alumina), steel, for example, a low carbon steel or a grade of stainless steel.

In some embodiments, the inert gas (e.g., nitrogen) in the calcination chamber is not static. In some embodiments, it is dynamic and flows over the precatalyst. Flow rates are a function of many variables such as the shape of the chamber, the size of the opening and exit ports of the chamber, the pressure drop across the inlets and outlets. One skilled in the art or having access to computational fluid dynamic programs can calculate flow rates. However, some starting point for the calculation is required. A starting point is the flow rate for a tubular drying chamber (tube) having a one inch (2.54 cm) internal diameter and a length of 152 cm (59.8 inches) is from 200-500 sccm per 30-250 gram of catalyst precursor. In some instances, the flow rate may be equivalent to a flow rate through a 1 inch diameter tubular drying chamber having a length of 152 cm from 250 to 450 sccm per 30-250 gram of catalyst precursor. However, the flow rate needs to be increased as the chamber volume increases.

The pressure in the interior of the flow chamber should be at least 1 psig (6.9 kPag) in some instances from 1 to 5 Psi, in some cases, higher than 5 psi.

The temperature of the gas flowing through the chamber is from 300° C. to 540° C. (in some cases from 400° C. to 525° C.). The temperature of the inert gas flowing over the catalyst is influenced by the temperature of the calcination and the flow rate.

In some embodiments, the catalyst precursor is held at the calcining temperature for at least 2 hours, or for example, from 2-24 hours and cooled to room temperature.

During the calcining process the catalyst precursor may be at least partially enclosed in a breathable or permeable covering. In some embodiments it is preferred that the covering substantially encloses the catalyst precursor (e.g. at least 50% or for example not less than 75% of the external surface of the catalyst precursor is covered by the breathable or permeable covering). The covering can have a permeability to gas from 5 cubic feet per minute (8.5 cubic meter/h) to 100 cubic feet per minute (170 cubic meter/hour) in some cases from 10 cubic feet per minute to 60 cubic feet per minute according to the measurement method specified by ASTM E2945-14. The permeable covering should have a melting point greater than 600° C. Provided the covering is breathable or permeable it may be a woven or nonwoven material. For example, it could be a plastic or metallic (or a metalized plastic substrate) substrate having a melting point above 600° C. Permeability could be provided by any mechanical means to permit the passage of gas through the covering such as needle type punching process. The permeable covering could be a non-woven chosen from polymers having a melting point above 600° C. and glass and mineral fiber, for example, glass and mineral fiber (e.g. fiber glass batting). If the covering is a woven fabric, the permeability would be controlled by the tightness of the weaving of the fabric. For example, the fabric could have up to 960 of pores per $cm^2$ for multifilament woven fabric.

In some embodiments activated carbon (greater than 90%, of for example greater than 95% purity) may be placed on top of the permeable covering to scavenge oxygen and materials released from the catalyst. The carbon may be used in amounts up to 0.5 g, typically 0.1 to 0.3 g per 1 g of catalyst precursor being calcined.

The catalysts prepared in accordance with the present disclosure have an x-ray diffraction pattern (XRD having) typically associated with a polycrystalline (broad reflection peaks) structure vs. predominantly crystalline material (narrow reflection peaks), which is characteristic of the classical catalyst. It is the common belief in the literature that the active phase is the crystalline MoVNbTeOx phase referred to as M1 (narrow reflection peaks) as opposed to the broad smoother reflection peaks of the present catalyst. The XRD for a typical ODH catalyst has the intense diffraction angles) at 2 Φ (Cu source) at 22° having a half height peak width from 19° to 21° and broad secondary peak at 28° having a half width from 25° to 33°. Generally, the typical ODH catalyst has a crystallite size (T) of about 90 nm. Whereas the Inventive Example has a crystallite size of from 45 nm to 55 nm, typically 48 to 52 nm, in some cases 50±1 nm. Crystallite size is calculated using the Scherrer equation, where K (dimensionless shape factor) is assumed to be 1, λ is the X-ray wavelength from Copper source and is 1.5406 Å, θ is the Bragg angle of 22.29°, and β is the line broadening at half the maximum intensity (FWHM) as determined for the XRD data.

The catalysts in accordance with the present disclosure demonstrate a higher amorphous component not less than 40 wt. %, in some embodiments not less than 50 wt. %, for example greater than 60 wt. % or for example greater than 70 wt. %.

The catalysts of the present disclosure have a smaller pore size than those of the base line. The catalysts made in accordance with the present process have a majority of pores having a size less than 10 nm. Catalysts prepared without the calcination of the present disclosure tend to have relatively flat pore size distribution.

In a further embodiment, from 10 wt. % to 95 wt. %, for example from 25 wt. % to 80 wt. %, or for example from 30 wt. % to 45 wt. %, of the catalyst is bound, agglomerated, filled, promoted, impregnated, or supported with from 5 wt. % to 90 wt. %, for example from 20 wt. % to 75 wt. %, or for example from 55 wt. % to 70 wt. % of a material (for example, a binder) other than active phase chosen from slurries of $TiO_2$, $ZrO_2$ $Al_2O_3$, $AlO(OH)$, $Nb_2O_5$ and mixtures thereof, where the slurries can be acidic, basic or neutral binder slurries, and provided that $ZrO_2$ is not used in combination with an aluminum containing binder.

In a further embodiment, there is provided a method for the oxidative dehydrogenation of a mixed feed including a $C_{2-4}$ paraffin (e.g., ethane) and oxygen in a volume ratio from 70:30 to 95:5 and optionally one or more $C_{3-6}$ alkanes or alkenes and oxygenated species including CO and $CO_2$ at a temperature greater than 320° C. up to than 385° C., a gas hourly space velocity of not less than 100 $hr^{-1}$, and a pressure from 0.8 to 7 atmospheres including passing said mixture over the above catalyst.

In a further embodiment, the ODH process has a selectivity to ethylene of not less than 85%.

In a further embodiment, the gas hourly space velocity of the ODH process is not less than 500 $hr^{-1}$ for example, not less than 1500 $hr^{-1}$ in some embodiments 3000 $hr^{-1}$.

In a further embodiment, the temperature of the ODH process is less than 375° C., for example, less than 360° C.

The catalysts prepared using the calcining procedure of the present disclosure are more robust than comparable catalysts prepared using a conventional calcination method (higher temperatures and no non-woven covering no carbon) and maintains it activity albeit as a slightly lower selectivity than a catalyst calcined in a conventional process. The catalysts may also be regenerated in situ in the oxidative dehydrogenation reactor by passing oxygen, air optionally in combination with one or more inert gasses over the catalyst.

In one embodiment, the present disclosure provides a method to calcine a catalyst precursor of the formula $Mo_1V_{0.1-1}Nb_{0.1-1}Te_{0.01-0.2}X_{0-2}O_d$ where X is chosen from Pd, Sb Ba, Al, W, Ga, Bi, Sn, Cu, Ti, Fe, Co, Ni, Cr, Zr, Ca and oxides and mixtures thereof, and d is a number to satisfy the valence of the catalyst while maintaining an amorphous content of not less than 40 wt. % including calcining the catalyst precursor in an inert container with flow passage there through, including heating the catalyst precursor at a rate from 0.5 to 10° C. per minute from room temperature to a temperature from 370° C. to 540° C. under a stream of pre heated gas chosen from steam and inert gas and mixtures thereof at a rate of flow comparable to a flow rate of not less 150 sccm through a 2.54 cm diameter tube, with a length of 152 cm at a pressure of greater than or equal to 1 psig having a temperature from 300° C. to 540° C. and holding the catalyst precursor at that temperature for at least 2 hours and cooling the catalyst precursor to room temperature the catalyst precursor being fully or partially enclosed by a porous material having a melting temperature greater than 600° C.

In a further embodiment, the present disclosure provides in combination with one or more other embodiments a method wherein the inert container is made from high temperature glass, quartz, ceramics, or steel.

In a further embodiment, the present disclosure provides in combination with one or more other embodiments a method wherein the inert container has a heat conductivity greater than 0.34 W $m^{-1}$·K.

In a further embodiment, the present disclosure provides in combination with one or more other embodiments a method wherein the flow rate of inert gas and mixtures thereof is greater than 150 sccm.

In a further embodiment, the present disclosure provides in combination with one or more other embodiments a method wherein the pressure of inert gas greater than 1 psig.

In a further embodiment, the present disclosure provides in combination with one or more other embodiments a method wherein the heat up rate is 0.9 to 2.0 C per min In a further embodiment, the present disclosure provides in combination with one or more other embodiments a method wherein the catalyst precursor is held at a temperature from 2-24 hours.

In a further embodiment, the present disclosure provides in combination with one or more other embodiments a method wherein the catalyst is held at a temperature from 400° C. to 525° C.

In a further embodiment, the present disclosure provides in combination with one or more other embodiments a method wherein the stream of inert gas and mixtures thereof includes nitrogen.

In a further embodiment, the present disclosure provides in combination with one or more other embodiments a method wherein the porous material is chosen from glass and mineral fiber.

In a further embodiment, the present disclosure provides in combination with one or more other embodiments a method wherein optionally charcoal or activated carbon is on an outer surface of the porous material in an amount up to 0.5 g per 1 g of catalyst precursor.

In a further embodiment, the present disclosure provides in combination with one or more other embodiments a method wherein X is one or more metals and oxides thereof are chosen from Pd, Sb, Ba, Al, Cu, Ti, Fe, Ca, Zr and mixtures thereof.

In a further embodiment, the present disclosure provides in combination with one or more other embodiments a method wherein the molar ratio of said one or more metals and oxides chosen from Pd, Sb, Ba, Al, Cu, Ti, Fe, Ca, Zr and mixtures thereof to Mo is from 1:0.001-0.3, for example, from 1:0.05-0.15.

In a further embodiment, the present disclosure provides in combination with one or more other embodiments a method wherein the X is chosen from one or more metals and oxides thereof are chosen from Pd, Sb, Ba, Al, Cu and mixtures thereof.

In a further embodiment, the present disclosure provides in combination with one or more other embodiments a method wherein in the catalyst precursor X is absent.

In a further embodiment, the present disclosure provides in combination with one or more other embodiments a catalyst precursor having the formula:

$$Mo_{1.0}V_{0.10-0.49}Te_{0.06-0.17}Nb_{0.13-0.19}O_d$$

In a further embodiment, the present disclosure provides in combination with one or more other embodiments a calcined catalyst of the formula:

$$Mo_1V_{0.40-0.45}Te_{0.10-0.16}Nb_{0.13-0.16}O_d.$$

In a further embodiment, the present disclosure provides in combination with one or more other embodiments a calcined catalyst of the formula $$MoV_{0.40-0.45}Te_{0.10-0.16}Nb_{0.13-0.16}O_d$$

having an amorphous content of not less than 40 wt. %.

In a further embodiment, the present disclosure provides in combination with one or more other embodiments a calcined catalyst having a crystallite size calculated according to the Scherrer equation of 45 to 55 nm.

In a further embodiment, the present disclosure provides in combination with one or more other embodiments a calcined catalyst having a crystallite size calculated according to the Scherrer equation of 50 to 52 nm.

In a further embodiment, the present disclosure provides in combination with one or more other embodiments a calcined catalyst bound, agglomerated, filled, promoted, impregnated, supported with from 5-90 wt. % of a material other than active phase.

In a further embodiment, the present disclosure provides in combination with one or more other embodiments a method for the oxidative dehydrogenation of a mixed feed including one or more $C_{2-4}$ paraffins and oxygen in a volume ratio from 70:30 to 95:5 and optionally one or more $C_{3-6}$ alkanes or alkenes and oxygenated species including CO and $CO_2$ at a temperature from 320° C. up to 385° C., a gas hourly space velocity of not less than 100 hr$^{-1}$, and a pressure from 0.8 to 7 atmospheres including passing said mixture over a catalyst as above.

EXAMPLES

An oxidative dehydrogenation catalyst was prepared using the following hydrothermal process.

Hydrothermal Synthesis:

259.4 g of $(NH_4)_6Mo_6TeO_2 \cdot 7H_2O$ (s) was dissolved in 600 mL of de-ionized water in a 2 L three neck round bottom flask (RBF), with a stir rate of 750 rpm with the addition of a warm water bath 189.11 g of $VOSO_4 \cdot 3.41H_2O_{(s)}$ was dissolved in 300 mL of de-ionized water, with the addition of a warm water bath 194.35 g of $H_3[NbO(C_2O_4)_3]_{(soln.)}$ was weighed into a 250 mL beaker and held for later use $VOSO_4 \cdot 3.41H_2O_{(aq)}$ solution was added to the $(NH_4)_6 Mo_6TeO_2 \cdot 7H_2O_{(aq)}$ solution in the 1 L RBF Solution turned black Solution was left to stir for 30 minutes, after which the solution turned a purple color All manipulations were performed in air 194.35 g of $H_3[NbO(C_2O_4)_3]_{(soln.)}$ was added to a 250 mL addition funnel, affixed to the 3 neck RBF Solution was added dropwise to the agitating purple slurry (60 minutes for addition time)

Solution remained as a dark purple slurry

Solution was transferred to a 1 L glass liner inside a 1 L PARR autoclave

Autoclave set up was sealed and purged 10 times with repeating $N2_{(g)}$ evacuation sequences Autoclave was connected to the condenser set up Reaction was left to stir overnight in the autoclave set up at room temperature The following day the PARR autoclave was hated to 175° C., the autoclave reached a temperature of 172° C. after 48 hours Reaction mixture was left to heat in the autoclave set up overnight at 175° C. with the condenser set up The following day the temperature was set back to room temperature Reaction set up was not cooled by the end of the day and was left to cool over the weekend After the reaction was cooled it was depressurized and filtered through 4× Whatmann 4 filter paper media The filter cake was rinsed with approximately 0.5 L of deionized water until the filtrate ran clear Filtration time was approximately 2 hours Filter dried catalyst was dried in the oven at 90° C. overnight Dried catalyst was ground and sieved Calcining Procedure Catalyst was loaded in four 25 g portions into quartz tube reactor (QRU). The QRU was purged under bulk nitrogen for several hours and then switched to purified nitrogen (bulk nitrogen passed through catalyst beds) for two days to ensure a sufficiently oxygen free environment for calcination. The purified nitrogen flow was 400 sccm. The heating program used was: RT to 600° C. in 6 hours and held at 600° C. for 2 hours, then cooled to room temperature by convective cooling.

Figure 1:
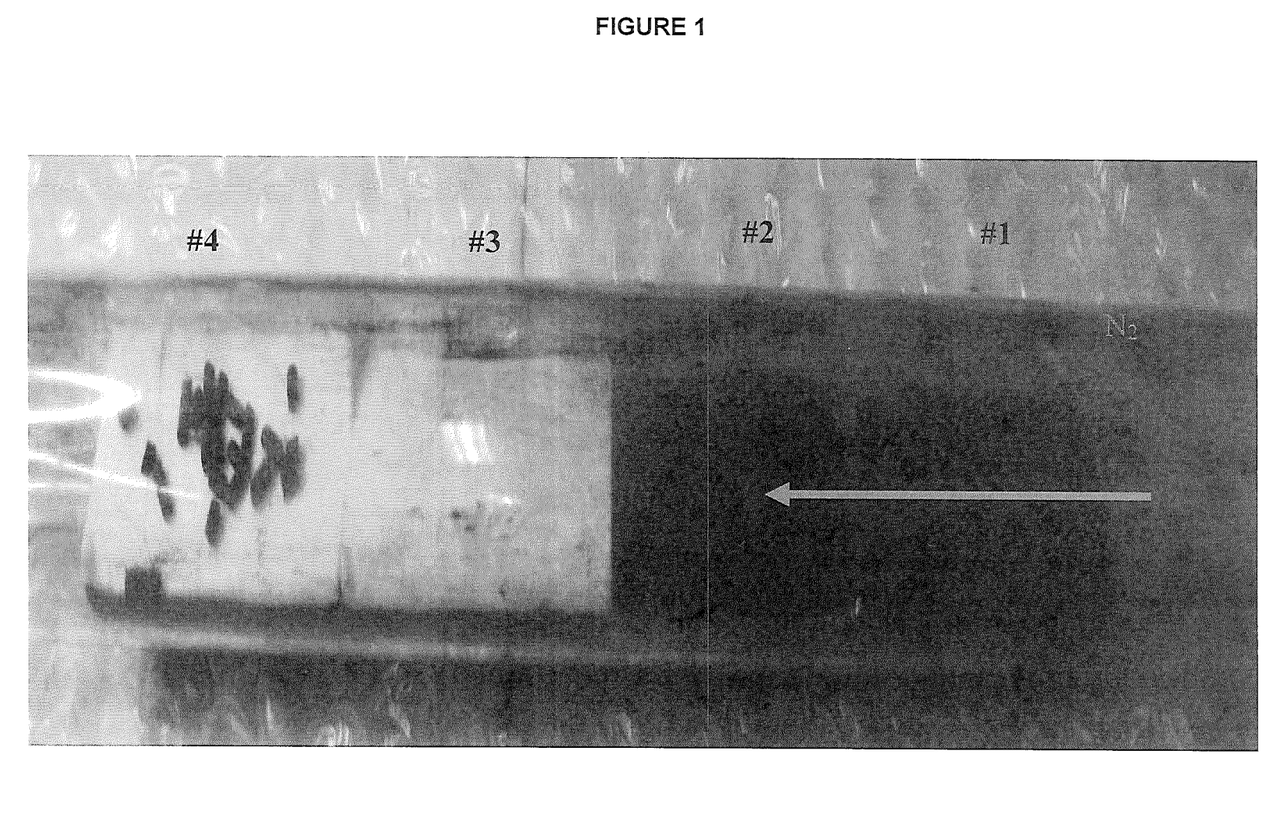
FIG. 1 is a diagram of the location of the samples of catalyst precursor in the quartz tube reactor showing the heating zones and the flow of nitrogen.

Four boats loaded with catalyst were loaded into quartz tube according to the scheme as shown in FIG. 1.

The heating zone where the 4$^{th}$ boat was located was not heated. The estimated temperature for calcination in boat 4 was from 400 to 525° C. The first two boats were calcined via the usual calcination procedure at 600° C. Boat #3 and #4 were covered with ceramic membrane material (glass wool), which resulted in lower flow of nitrogen above (over) the catalyst precursor. Additionally, activated carbon was placed on the top of the ceramic membrane material over boat 4 to scavenge any oxygen released from the surface of non-calcined catalyst.

Figure 2:
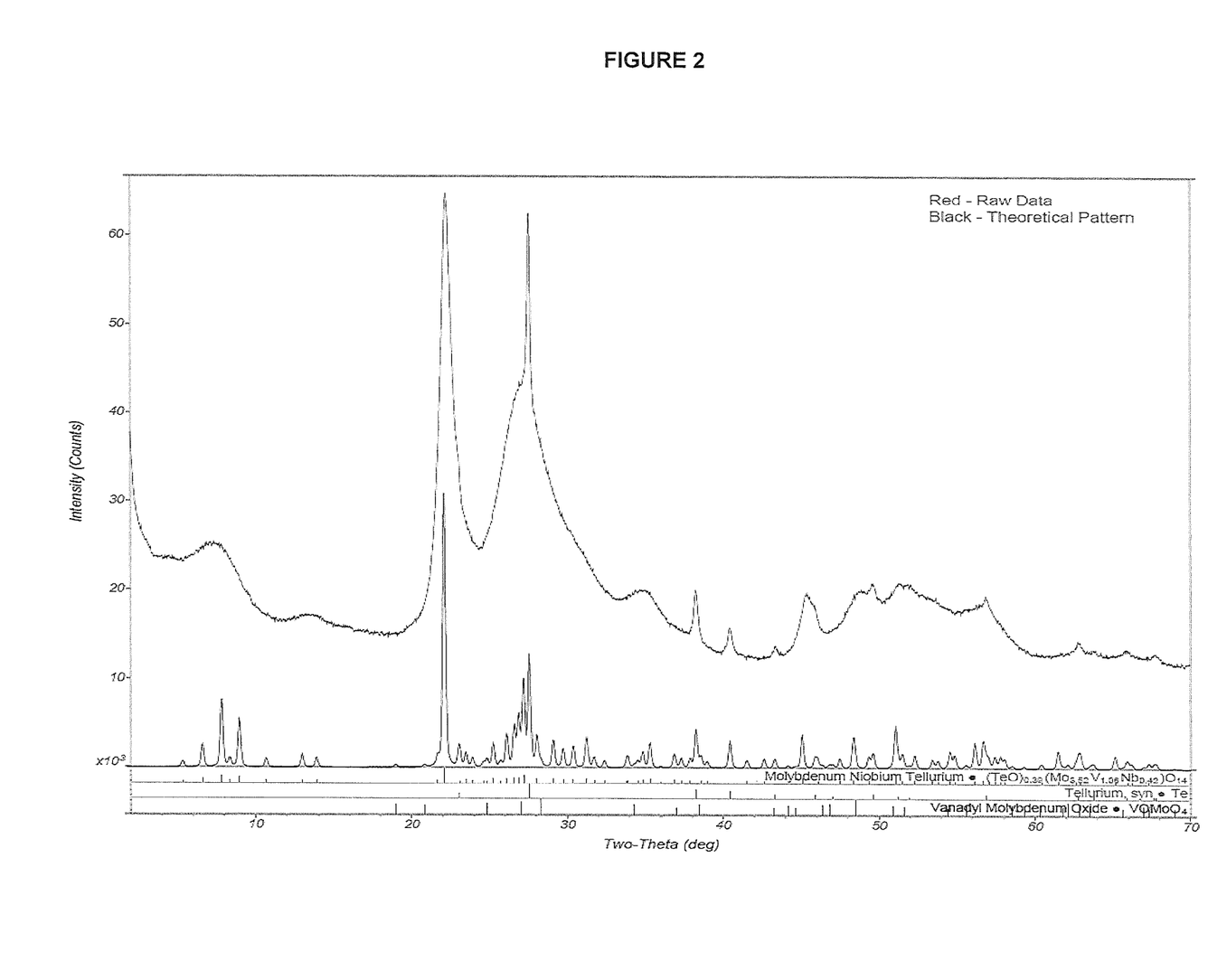
FIG. 2 is an XRD of an uncalcined (low calcined) catalyst of boat 4 with an underlying base line for the calcined sample.

FIG. 2 is an X ray diffraction pattern (XRD) for the uncalcined catalyst sample. The figure also contains a baseline of an XRD of a typical calcined catalyst. In FIG. 2 the relatively sharper peak to the left side of the XRD is the M1 phase. The larger broader peek to the right is the M2 phase. The sample of low or partially calcined catalyst from boat 4 has a broader M2 peek than that of a calcined catalyst.

The catalyst produced from boat 4 was tested in a lab scale dehydrogenation reactor (Micro reactor unit—MRU) and the results are compared to a conventional calcination process. The results are set forth in Table 1.

TABLE 1

Activity and Selectivity Comparison Between Baseline Example and Inventive Example at 25% Conversion

|  | Inventive Example | Baseline Example |
|---|---|---|
| Temperature at 25% conversion | 330° C. | 380° C. |
| Selectivity at 25% conversion † | 87% | 98% |

The catalyst calcined in accordance with the procedures of the current application were tested in a long term oxidative dehydrogenation reactor together with two baseline samples (a conventionally calcined catalyst and an un-calcined catalyst). The results are set forth in table 2 below.

The un-calcined catalyst had good conversion—25% conversion at 340° C. which is very completive with the conversion for the sample in accordance with the present disclosure (low calcined catalyst). However, the catalyst died after about 8 hours testing.

The testing shows the catalyst calcined in accordance with the present application has a better stability than the baseline catalyst and is fully regeneratable with oxygen.

Figure 3:
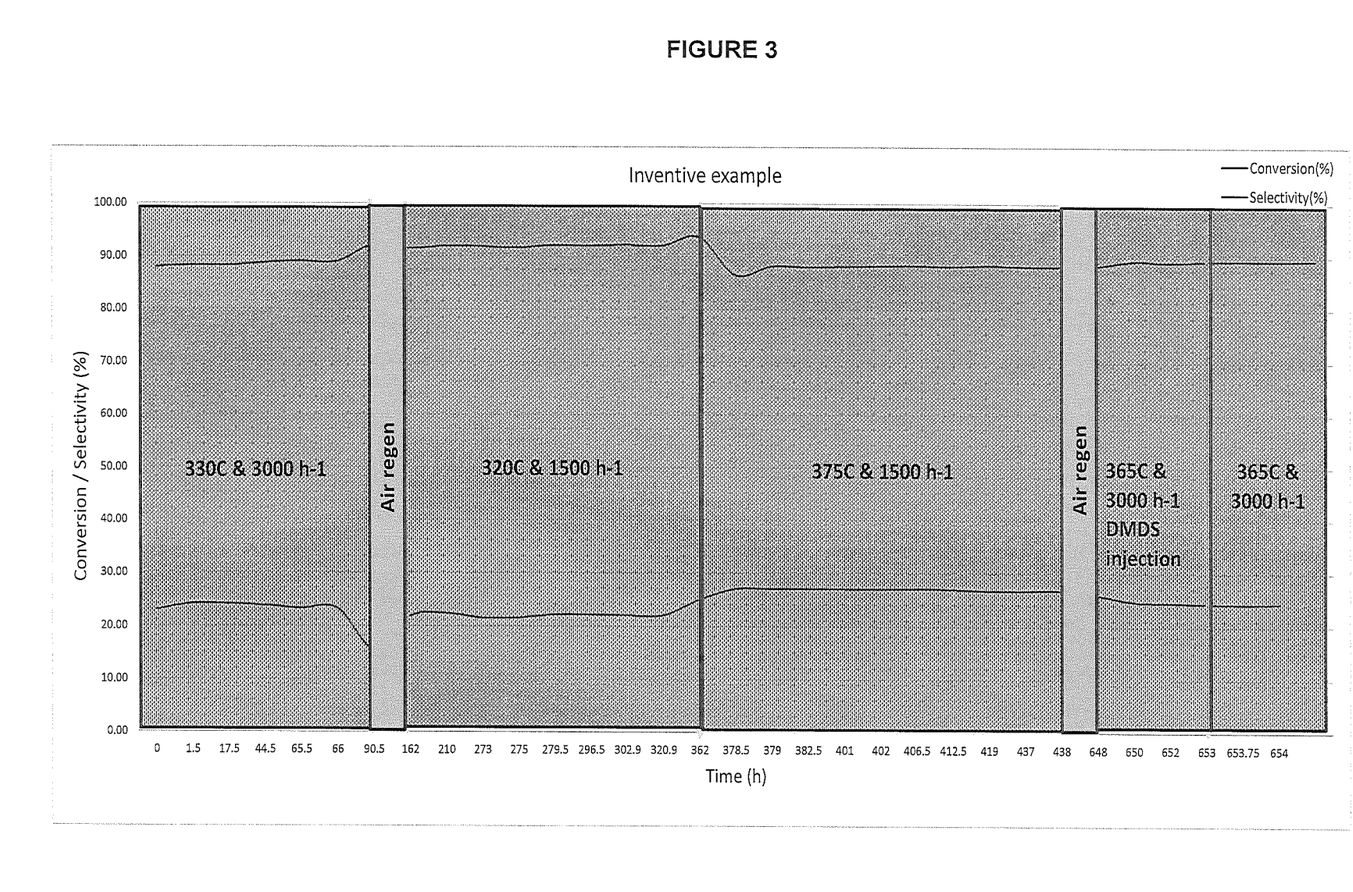
FIG. 3 is a plot of the conversions and selectivity of the catalyst for ethane to ethylene at various temperatures over a long term run of about 650 hours.

A sample of catalyst obtained from boat 4 was in a micro reactor unit (MRC) ethane oxidative dehydrogenation unit in a longer term run with several in situ air regenerations of the catalyst. The results are shown in FIG. 3. In FIG. 3, the upper line is the selectivity to ethylene at 25% conversion and the lower line is conversion at the temperature specified in the sections of the graph. At 300° C. the conversion is slightly below 25%. At 320° C. the conversion is slightly below 25%. The temperature of the reactor was increase to 375° C. so that there was no residual oxygen the product stream leaving the reactor. At 375° C. the conversions is around 28%. For part of the experiment dimethyl disulphide (DMDS) was injected with the feed. And the temperature was reduced to 356° C. and the conversion dropped slightly. Throughout the run the selectivity was in the 88 to 90% range.

The number following the temperature is hourly space velocity of the feed gas (ethylene and oxygen). The vertical darker bars show air regeneration.

The catalyst showed excellent stability/robustness even on regeneration and in the presence of DMDS.

Figure 4:
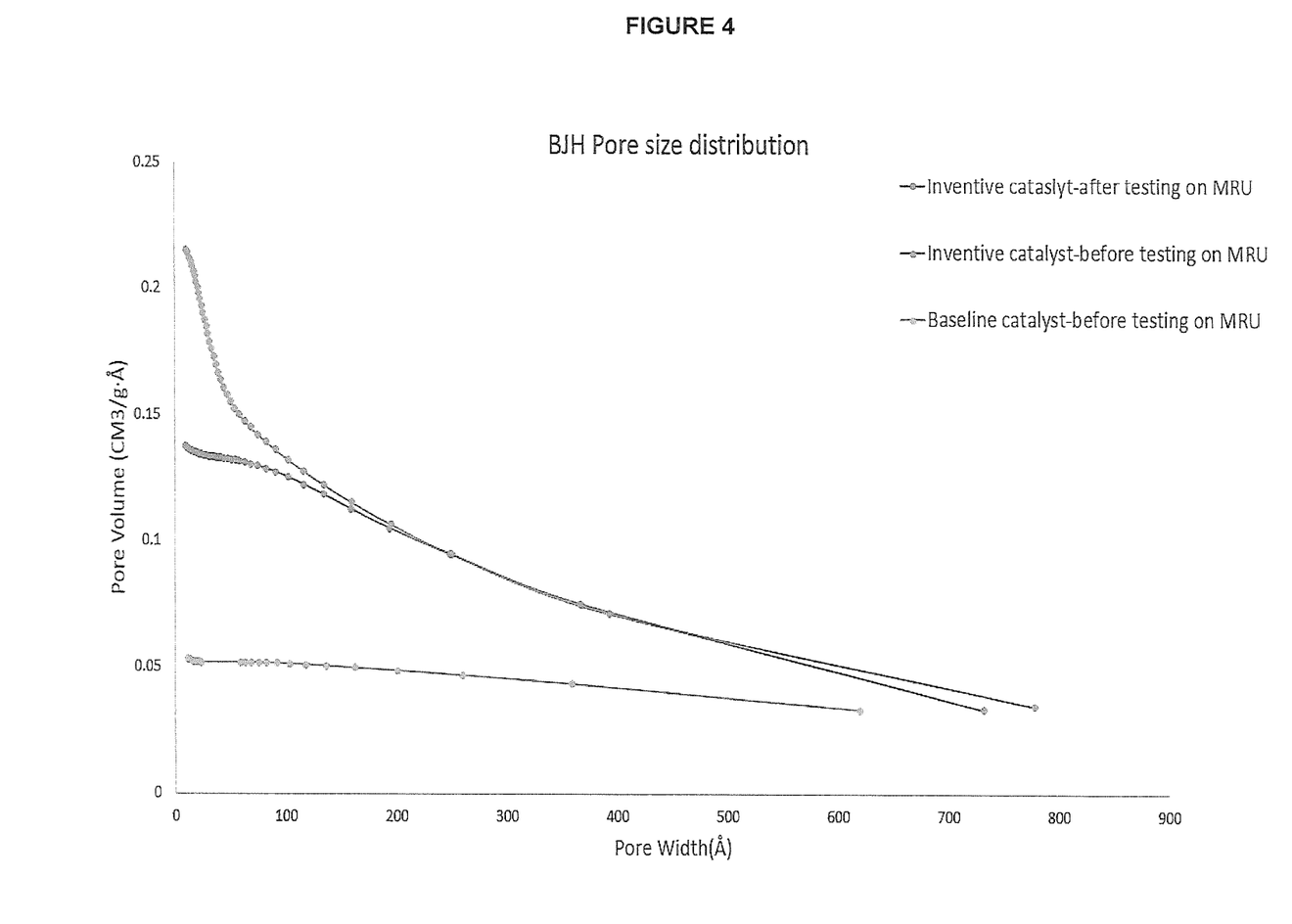
FIG. 4 is plot of the pore size distribution of the catalysts of the present disclosure.

The pore size of the base line catalyst and the catalyst of the present disclosure before and after testing in an ethylene dehydrogenation unit were measured using BET. The results are shown in FIG. 4. The results show the catalyst according to the present disclosure has majority of small pores less than 10 nm. After testing the volume of pores less than 10 nm has decreased but is still larger than the base line catalyst. In use the pore size of the base line catalyst is further reduced.

The following table show the reaction conditions and results for the trial.

TABLE 2

Summary of Performance Comparisons Between Inventive Example and Conventionally Calcined Catalyst and Un-Calcined Catalyst

| Conditions | Inventive Example | Conventionally Calcined Catalyst | Un-calcined catalyst |
|---|---|---|---|
| Conversion and selectivity of fresh catalyst (Reference Point) | 25% conversion is at 330° C. and 3000 h$^{-1}$ space velocity with selectivity 87% | 24% conversion is at 367° C. and 3000 h$^{-1}$ with 97% selectivity | After 8 h, temperature at 21.6 wt. % conversion increased from 340 C. to 370 C., with selectivity toward ethylene decreased from 82.7 wt % to 77.35 wt % |
| Stability (before changing of conditions) | No changes to conversion and selectivity at 25% ethane conversion after 150 hours on stream at conditions above | Conversion decreased by 5% and selectivity dropped by 2.43% after 193 h run length | Did not last longer than 8h |
| Oxygen depletion condition (Testing catalyst to low O$_2$ content in the product, i.e. less than 100 ppm) | No changes to conversion and selectivity after 60 hours on stream after back to original conditions | Both conversion and selectivity decreased by 3.5% at 367° C. after 259 hours on oxygen depleting condition | NA |
| Air regen (Regen done after conditions are changed, i.e. exposed to oxygen depleted conditions. | Air regens fully recover the catalyst performance, even after oxygen depleting environment operation | Air regen did not result in a full recovery of the original catalyst performance but rather results in noticeable decrease of selectivity toward ethylene over time |  |

TABLE 3

Long Term Oxidative Dehydrogenation of Ethane on Microreactor Unit (MRU) Using Inventive Catalyst

| Reactor conditions and rational behind the condition changes | Day(s) | space velocity ($h^{-1}$) | Reactor Unit Temperature Range (° C.) min | max | Conversion Range (%) min | max | Selectivity Range (%) min | max | 25% Conversion Temperature (° C.) | Selectivity at 25% Conversion |
|---|---|---|---|---|---|---|---|---|---|---|
| Screening and establishing standard run conditions (25% Conversion Temperature at 3000 h−1 space velocity) | Day 1 | 3000 | 280 | 330 | 8.04 | 24.15 | 88.26 | 92.80 | 332 | 87.5 |
| Held run at stable conditions of 330 C. for 5 days Activity decreased from 24.15 to 23.30% conversion | Days 2-6 | 3000 | 330 | | 23.30 | 24.15 | 88.26 | 89.09 | | |
| Air regen: 380 C. at 250 sccm for 5 h then decrease to 320 C. and leave it under air overnight. | Day 6 | | 380 | | | | | | | |
| Re-establishing standard run conditions (25% Conversion Temperature at 3000 h−1 space velocity) | Day 7 | 3000 | 280 | 355 | 6.59 | 25.00 | 89.43 | 96.97 | 355 | 89.43 |
| Started to decrease feed gas flow to target no residual oxygen left on outlet of reactor | Day 8 | 1500 1070 | 280 320 | 320 | 8.64 25.02 | 22.75 | 91.96 91.64 | 95.91 | | |
| | Day 9-10 | 1070 | 320 | | 25.02 | 26.58 | 91.16 | 91.64 | | |
| Left under stable no residual oxygen conditions for 5 days | Day 10-15 | 1500 | 320 | | 21.57 | 22.18 | 91.48 | 92.21 | | |
| Re-establishing standard run conditions (25% Conversion Temperature at 3000 h−1 space velocity) | Day 15 | 3000 | 320 | 355 | 12.83 | 25.01 | 89.74 | 93.7 | 355 | 89.74 |
| Allowed reactor to run under standard conditions over night | Day 16 | 3000 | 355 | | 24.43 | | 89.91 | | | |
| Started to increase temperature to target no residual oxygen left on outlet of reactor | Day 16 | 3000 | 355 | 375 | 24.43 | 26.8 | 86.51 | 89.91 | | |
| Left under stable no residual oxygen conditions for 7 days | Days 16-23 | 3000 | 375 | | 26.72 | 27.05 | 88.04 | 88.4 | | |
| Re-establishing standard run conditions (25% Conversion Temperature at 3000 h−1 space velocity) | Day 23 | 3000 | 355 | 375 | 21.46 | 26.76 | 88.33 | 89.51 | 365 | 88.9 |
| Air regen: 380 C. at 250 sccm for 5 h then decrease to 320 C. and leave it at this temperature under air overnight. | Day 23 | | 380 | | | | | | | |
| Re-establishing standard run conditions (25% Conversion Temperature at 3000 h−1 space velocity) | Day 24 | 3000 | 300 | 368 | 8.57 | 25.48 | 88.65 | 96.77 | 364 | 88.8 |
| Held under air at 300 C. over weekend to avoid consuming ethane | Day 24-26 | | 300 | | | | | | | |
| Re-establishing standard run conditions (25% Conversion Temperature at 3000 h−1 space velocity) | Day 26 | 3000 | 330 | 365 | 15.06 | 25.17 | 88.88 | 92.27 | 364 | 88.9 |
| Allowed reactor to run under standard conditions for 3 days before DMDS injection | Day 26-30 | 3000 | 365 | | 25.95 | | 89.06 | | | |
| Conditions during DMDS injection | Day 30 | 3000 | 365 | | 24.42 | 24.76 | 89.06 | 89.31 | | |
| Conditions after DMDS injection | Day 30 | 3000 | 365 | | 24-29 | 24.36 | 89.28 | 89.4 | | |

Testing was carried out over 30 days under various conditions (no residual oxygen or exposure to sulfur-containing environments) to demonstrate robustness of catalyst. Standard conversion conditions were established at start of run to create a reference point, i.e. at 3000 h⁻¹ flow, what temperature is needed to achieve 25% conversion. After catalyst was exposed to unfavorable conditions, the reference conditions were revisited to see what temperature was needed to achieve 25% conversion. Re-establishing the reference conditions provided a means of evaluating how the catalyst was responding to testing. An increase in 25% conversion temperature is acceptable as long as the temperature stays the same/below the threshold value (conversion temperature of standard catalyst) and has selectivity that is better than a standard catalyst run over similar long-term and oxygen-deprived conditions.

What is claimed is:

1. A method for oxidative dehydrogenation of a mixed feed comprising one or more $C_{2-4}$ paraffins and oxygen in a volume ratio from 70:30 to 95:5 at a temperature from 320° C. up to 385° C., a gas hourly space velocity of not less than 100 hr⁻¹, and a pressure from 0.8 to 7 atmospheres comprising passing the mixed feed over a catalyst of formula $$Mo_1V_{0.1-1}Nb_{0.1-1}Te_{0.01-0.2}X_{0-2}O_d$$

where X is chosen from Pd, Sb, Ba, Al, W, Ga, Bi, Sn, Cu, Ti, Fe, Co, Ni, Cr, Zr, Ca, oxides thereof and mixtures thereof, and d is a number to satisfy valence of the catalyst, wherein the mixed feed comprises at least one of carbon monoxide (CO) or carbon dioxide ($CO_2$).

2. The method of claim 1, wherein the mixed feed comprises at least one of $C_{3-6}$ alkanes or alkenes.

3. The method of claim 1, wherein X is one or more metals and oxides thereof chosen from Pd, Sb, Ba, Al, Cu, Ti, Fe, Ca, Zr and mixtures thereof.

4. The method of claim 3, wherein a molar ratio of the one or more metals and oxides chosen from Pd, Sb, Ba, Al, Cu, Ti, Fe, Ca, Zr and mixtures thereof to Mo is from 1:0.001-0.3.

5. The method of claim 4, wherein X is the one or more metals and oxides thereof chosen from Pd, Sb, Ba, Al, Cu and mixtures thereof.

6. The method of claim 1, wherein in the catalyst, X is absent.

7. The method of claim 6, wherein the catalyst has the formula:

$$Mo_{1.0}V_{0.10-0.49}Te_{0.06-0.17}Nb_{0.13-0.19}O_d.$$

8. The method of claim 1, wherein the catalyst comprises a calcined catalyst prepared by:

calcining a catalyst precursor of same formula in an inert container with flow passage there through, at a rate from 0.5 to 10° C. per minute from room temperature to a holding temperature from 370° C. to 540° C. under a stream of pre heated gas chosen from steam and inert gas and mixtures thereof at a flow rate of not less than 150 sccm at a pressure of greater than or equal to 1 psig, the stream of pre heated gas having a temperature from 300° C. to 540° C.;

holding the catalyst precursor at the holding temperature for at least 2 hours; and cooling the catalyst precursor to room temperature, the catalyst precursor being fully or partially enclosed by a porous material having a melting temperature greater than 600° C.

9. The method of claim 8, wherein the inert container is made from glass, quartz, ceramics, or steel, wherein the inert container has a heat conductivity greater than 0.34 W·m⁻¹·K, and wherein the porous material is chosen from glass and mineral fiber.

10. The method of claim 8, wherein the rate for heating the catalyst precursor is 0.9 to 2.0° C. per min.

11. The method of claim 8, wherein the catalyst precursor is held at the holding temperature from 2-24 hours.

12. The method of claim 11, wherein the holding temperature is from 400° C. to 525° C.

13. The method of claim 8, wherein charcoal or activated carbon is present on an outer surface of the porous material in an amount up to 0.5 g per 1 g of catalyst precursor.

14. A method for oxidative dehydrogenation of a mixed feed comprising one or more $C_{2-4}$ paraffins and oxygen in a volume ratio of the one or more $C_{2-4}$ paraffins to oxygen from 70:30 to 95:5 at a temperature from 320° C. up to 385° C., a gas hourly space velocity of not less than 100 hr⁻¹, and a pressure from 0.8 to 7 atmospheres comprising passing the mixed feed over a calcined catalyst of formula $$MoV_{0.40-0.45}Te_{0.10-0.16}Nb_{0.13-0.16}O_d$$

having an amorphous content of not less than 40 wt. %, and having a crystallite size calculated according to Scherrer equation of 45 to 55 nm.

15. The method of claim 14, wherein the mixed feed comprises at least one of carbon monoxide (CO) or carbon dioxide ($CO_2$).

16. The method of claim 14, wherein the mixed feed comprises one or more $C_{3-6}$ alkanes or alkenes.

17. The method of claim 14, wherein the calcined catalyst having a crystallite size calculated according to the Scherrer equation of 50 to 52 nm.

18. The method of claim 14 wherein the calcined catalyst is bound, agglomerated, filled, promoted, impregnated, or supported with from 5 to 90 wt. % of a material other than active phase.

* * * * *